United States Patent
Berry et al.

(10) Patent No.: US 6,206,910 B1
(45) Date of Patent: Mar. 27, 2001

(54) COMPLIANT INTRALUMINAL STENTS

(75) Inventors: Joel L. Berry, Winston-Salem, NC (US); James E. Moore, Miami, FL (US)

(73) Assignee: Wake Forest University, Winston-Salem, NC (US)

( * ) Notice: Subject to any disclaimer, the term of this patent is extended or adjusted under 35 U.S.C. 154(b) by 0 days.

(21) Appl. No.: 08/927,907

(22) Filed: Sep. 11, 1997

(51) Int. Cl.[7] .......................................... A61F 2/06
(52) U.S. Cl. .......................................... 623/1.15
(58) Field of Search .................... 623/1, 1.1, 1.11, 623/1.15, 1.16, 1.35; 606/198, 194

(56) References Cited

U.S. PATENT DOCUMENTS

| 5,496,365 | 3/1996 | Sgro | 623/1 |
| 5,593,442 | * 1/1997 | Klein | 623/12 |
| 5,630,829 | 5/1997 | Lauterjung | 606/198 |
| 5,755,781 | * 5/1998 | Jayaraman | 623/1 |
| 5,853,419 | * 12/1998 | Imran | 606/191 |
| 5,855,600 | 1/1999 | Alt | 623/1 |
| 5,861,025 | * 1/1999 | Boudghene et al. | 623/1 |
| 6,007,574 | * 12/1999 | Pulnev et al. | 623/1 |

* cited by examiner

Primary Examiner—David J. Isabella
Assistant Examiner—Alvin Stewart
(74) Attorney, Agent, or Firm—Dann, Dorfman, Herrell & Skillman, P.C.

(57) ABSTRACT

An expandable, intraluminal tubular stent is provided for insertion and expansion within the lumen of a vessel. The stent includes a plurality of longitudinal struts. A series of arcuate or V-shaped end links are connected between the ends of the longitudinal struts. A series of deformable cross-links are circumferentially connected between adjacent longitudinal struts at a center portion of the longitudinal struts to permit the stent to be expanded from a first smaller diameter into a second larger diameter upon insertion into the vessel.

47 Claims, 7 Drawing Sheets

COMPLIANT INTRALUMINAL STENTS

FIELD OF THE INVENTION

The present invention relates to a stent for placement within the lumen of a vessel and, more particularly, to an intraluminal stent having end configurations that improve compliance matching of relative flexibility between the stent and the vessel to minimize flow disturbance and stress concentration in the artery wall.

BACKGROUND OF THE INVENTION

Intraluminal, vascular stents have been widely used as solid mechanical, structural supports to maintain an open lumen following balloon angioplasty. However, there is a great deal of evidence that suggests that the mechanical environment in arteries plays an important role in the development and progression of cardiovascular disease. The presence of a vascular stent within the lumen of a vessel alters fluid flow patterns through the vessel. Accordingly, the use of stents may significantly influence the incidence of cardiovascular disease following balloon angioplasty due to changes in the mechanical environment caused by the stent.

From a mechanical perspective, arteries are quite complex. The arterial wall is subjected to internal pressurization that also induces large, circumferentially oriented stresses. In addition, the flow of blood through the artery creates a frictional shearing stress in the direction of flow. All of these stresses depend heavily on the arterial geometry, and thus vary greatly throughout the cardiovascular system. The presence of arterial grafts or stents provokes changes in these mechanical factors that may be important in determining the success of such grafts or stents.

Data are now emerging that implicate a mismatch in vessel compliance (i.e., the ratio of a change in vessel cross-sectional area to a change in vessel pressure) between the vascular graft or stent and the host vessel as a culprit in neointimal hyperplasia. Compliance mismatch is a mismatch in mechanical properties that results when a relatively rigid stent is inserted within a more flexible vessel. Compliance mismatch is a particular problem at the ends of the stent where the radial flexibility of the vessel abruptly changes due to the rigidity of an expanded stent. One of the consequences of compliance mismatch in a vessel is local blood flow alteration. For example, the presence of the stent in the vessel produces complex flow patterns that include vortices, which may lead to platelet activation, and flow stagnation, which may be related to platelet adhesion through increased near-wall particle residence time. Accordingly, a substantial mismatch between the circumferential compliance of arterial grafts or stents and contiguous native vessels may be deleterious to vessel patency. Accordingly, it would be desirable to reduce the problems associated with compliance mismatch.

SUMMARY OF THE INVENTION

In accordance with the present invention, an expandable, intraluminal stent is provided for deployment in a body passage, such as a blood vessel, to inhibit vessel stenosis. The stent in accordance with the present invention has a gradual change in radial flexibility along the longitudinal axis of the stent, in order to minimize flow disturbance and stress concentration in the artery wall, while still providing a relatively high radial strength enabling the stent to counteract elastic recoil of the vascular wall. In this regard, the stent in accordance with the present invention has increased radial flexibility at the outer ends to better match the flexibility or resiliency of the adjacent vessel while maintaining increased rigidity along the central portion of the stent to provide sufficient radial support to the vessel to inhibit vessel collapse or occlusion. In addition, the stent is easy to deploy, may be made of metal so that it can be imaged during deployment, and demonstrates a high expansion ratio. Furthermore, because of its unique configuration, the stent does not foreshorten along the longitudinal direction following expansion.

In a specific embodiment, a tubular stent includes a plurality of end links disposed in a ring at each end of the stent. Each end link is generally arcuate or V-shaped having a pair of legs joined at a central fulcrum. The tubular stent also includes a plurality of rigid longitudinal struts. The longitudinal struts are oriented generally parallel to one another about a central axis of the stent. The legs of the end links are connected to the ends of the longitudinal struts. The legs of a single end link are connected to the ends of adjacent longitudinal struts at one end of the stent.

At least one deformable link is circumferentially oriented around a central portion of the stent. The deformable link includes a plurality of individual V-shaped cross-links connected circumferentially between adjacent longitudinal struts. The length of the legs of the V-shaped cross-links can be changed to alter the rigidity of the expanded stent. The deformable cross-links enable the stent to be expanded from a first smaller diameter into a second larger diameter while providing sufficient rigidity to inhibit collapse of the vessel. The cross-links may have shorter legs than the legs of the end links so that shorter moment arms are provided by the cross-links so that the cross-links become more rigid than the end links.

The rigid longitudinal struts prevent longitudinal shrinkage of the stent during stent expansion. Toward this end, the longitudinal struts extend generally from one end of the stent to the other end of the stent. However, for applications where longitudinal foreshortening is not a problem or when greater longitudinal flexibility or greater radial flexibility about a central portion of the stent is desired, the longitudinal struts may span only part of the overall length of the stent. In a specific embodiment, one longitudinal strut can extend from one end of the strut toward a central portion of strut along one side of the tubular stent while another longitudinal strut extends from the other end of the stent toward a central portion of the stent along the opposite side of the tubular stent.

The end links are positioned with the legs oriented in an outward longitudinal direction to form moment arms so that radial flexibility of the end portions of the stent is increased. The stent permits a gradual change in radial flexibility from an end portion of the stent to the central portion of the stent to provide improved compliance matching between the stent and the vessel. The length of the legs of the end links may be changed to alter the radial flexibility of the stent for better compliance matching with the vessel.

BRIEF DESCRIPTION OF THE DRAWINGS

The foregoing summary, as well as the following detailed description of the preferred embodiments of the present invention, will be better understood when read in conjunction with the accompanying drawings, in which.

DETAILED DESCRIPTION OF THE PREFERRED EMBODIMENTS

Figure 1:
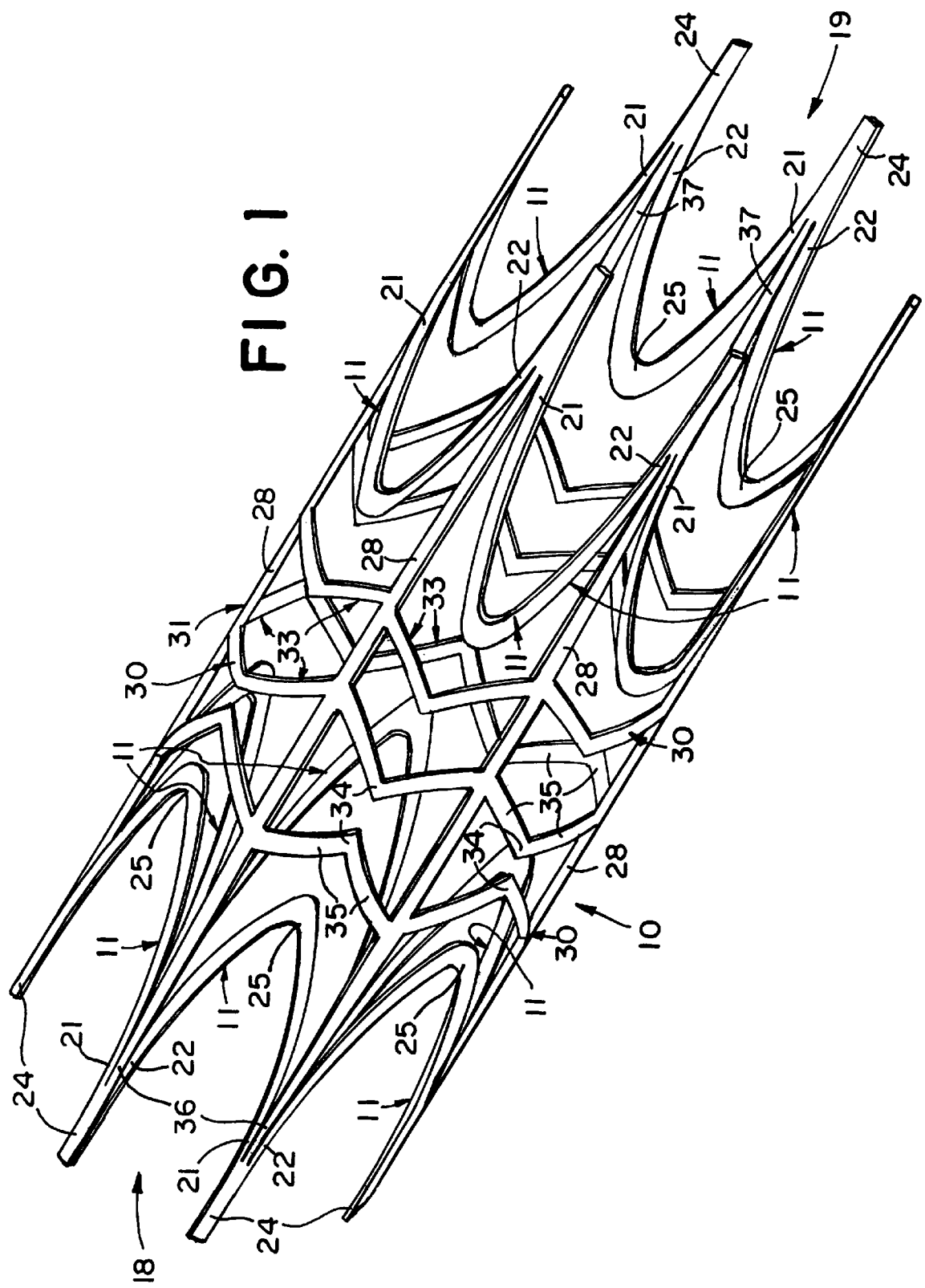
FIG. 1 is an enlarged perspective view of an expandable intraluminal stent shown in an expanded configuration in accordance with the present invention.
Figure 2:
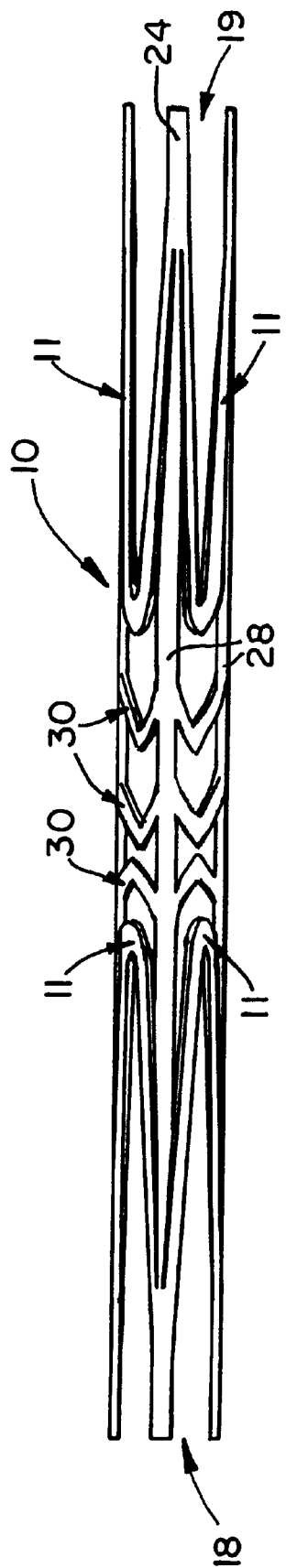
FIG. 2 is an enlarged, side elevational view of the stent of FIG. 1 shown in its unexpanded configuration.
Figure 3:
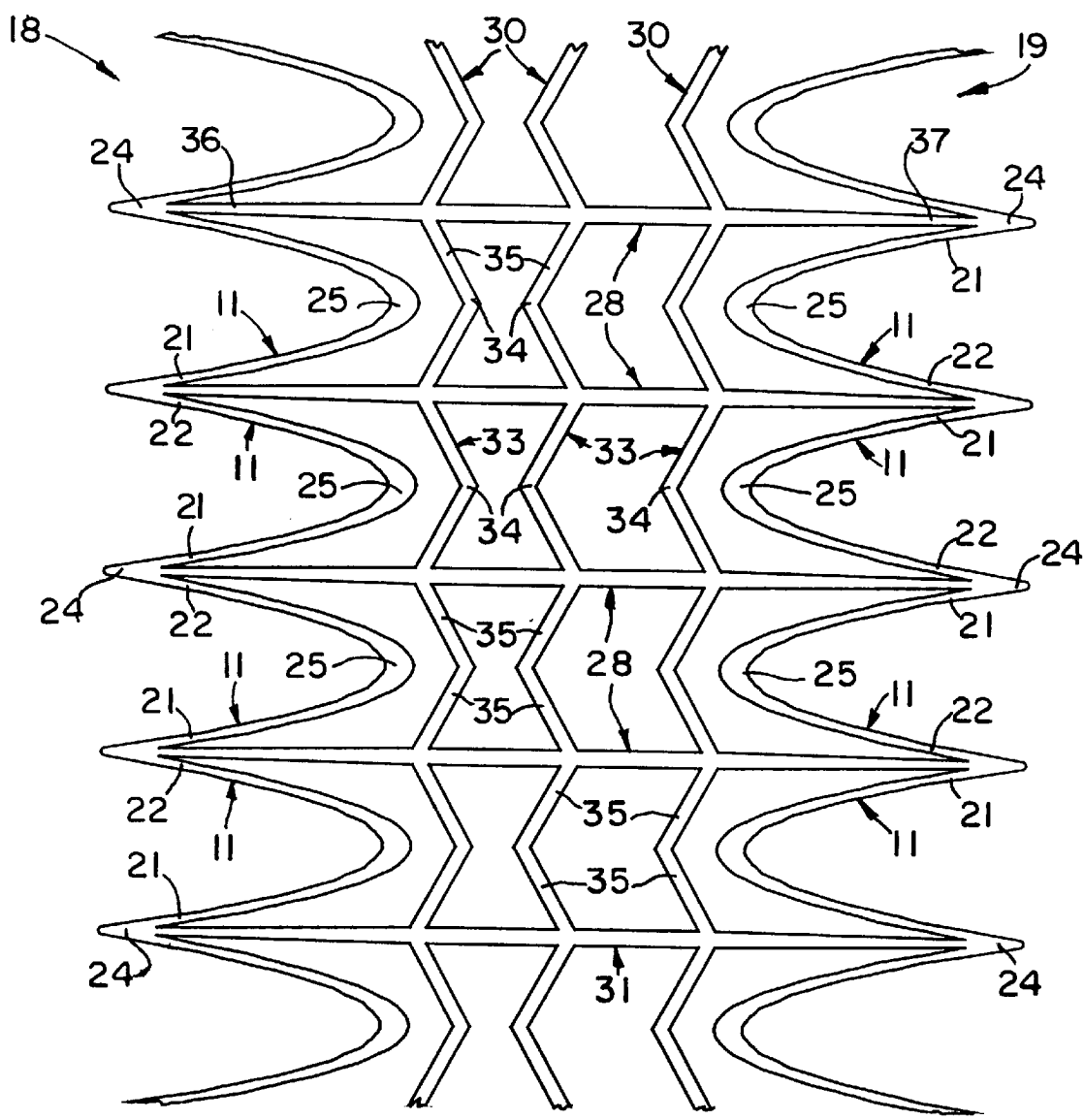
FIG. 3 is a partial cut-away view of the stent of FIG. 1 shown in a flattened, expanded configuration obtained by cutting the stent along longitudinal cutting planes.

Referring to FIGS. 1–3, an intraluminal stent 10 is depicted in the form of a generally tubular mesh-like configuration providing a central lumen along its central longitudinal axis. The generally tubular stent 10 includes a series of arcuate or V-shaped semi-rigid end links 11 which are disposed in a generally similar arrangement at each end, 18 and 19, of the tubular stent 10. The end links 11 of the stent 10 are generally equally spaced around the circular periphery at each end, 18 and 19, of the stent 10 with a first end 21 of each link 11 being joined at an end of a longitudinal rigid strut 28 adjacent a second end 22 of an adjacent link 11. Preferably, the first end 21 of each end link 11 is connected to the second end 22 of the adjacent link 11 at a junction 24 formed at the end of a longitudinal strut 28. In order to minimize the risk of puncturing the vessel, the junctions 24 are configured so that the tips of the junctions 24 are blunted in shape and do not form a sharp point at the ends of the longitudinal struts 28. As shown in FIG. 1, the junctions are generally frustoconical or frustopyramidical in shape so that sharp tips are not formed.

The links 11 at each end, 18 and 19, of the stent 10 are positioned adjacent to one another in a generally annular arrangement around the periphery of each end, 18 and 19, of the stent 10. Accordingly, each end link 11 at one end 18 of the stent 10 has an opposite end link 11 symmetrically positioned at the other end 19 of the stent 10. Although the depicted embodiment comprises six end links 11 disposed at each end, 18 and 19, of the stent 10, viable stent designs having more or less than six links at each end are possible.

The end links 11 are plastically deformable and have a general arcuate shape with first and second legs, 21 and 22, joined at a central fulcrum 25. As shown in FIG. 1, the end links are in a generally parabolic or semi-oval shape. The shape of the links 11 is chosen so that the legs, 21 and 22, of the links 11 flex about the central fulcrum 25 thereby creating a moment arm that enables radial flexibility of the stent 10 to be greatest at the ends, 18 and 19, of the stent 10. Towards that end, as best seen in FIG. 3, the width of each link 11 is greatest at the fulcrum 25 and tapers toward the outer ends of the legs, 21 and 22.

Rigid longitudinal struts 28 connect each end link 11 at one end 18 of the stent 10 so that a corresponding end link 11 is connected at the other end 19 of the stent 10. As best shown in FIG. 3, junctions 24 formed between adjoining end links 11 at the first end 18 of the stent 10 are symmetrically disposed relative to junctions 24 at the second end 19 of the stent 10. The longitudinal struts 28 serve as non-deformable struts to prevent the stent 10 from foreshortening along its longitudinal axis during expansion or collapse of the stent. Each longitudinal strut 28 thereby serves to maintain the junctions between the end links and the longitudinal struts at opposite ends, 18 and 19, of the stent 10 in relative longitudinal position along the longitudinal axis of the tubular stent 10. The longitudinal struts 28 are also sufficiently rigid to resist bowing or bending in the circumferential direction relative to the stent 10 while providing sufficient radial flexibility or resiliency to permit compliance matching with the vessel at the ends, 18 and 19, of the stent 10.

At least one deformable circumferential link 30 in the form of a series of plastically-deformable, wire-like cross-links 33 is provided circumferentially about a central portion 31 of the stent 10 to circumferentially interconnect the longitudinal struts 28. A plurality of generally parallel circumferential rows of links 30 may be used. The cross-links 33 in each circumferential link 30 permit the stent 10 to be diametrically expanded through plastic deformation of the cross-links 33. Accordingly, the stent 10 can be expanded from a first smaller diameter as shown in FIG. 2 to, or beyond, a second larger diameter as shown in FIG. 1.

As shown in FIGS. 1–3, the generally tubular, intraluminal stent 10 comprises three rows of circumferential links 30 positioned generally in parallel around a central portion of the stent. Each circumferential row of links 30 comprises a plurality of deformable, V-shaped cross-links 33 connected between adjacent longitudinal struts 28. As shown in FIG. 3, the V-shaped cross-links 33 disposed along one of the outer rows are oriented in the same direction as the V-shaped cross-links 33 along the center row whereas the V-shaped cross-links 33 on the remaining outer row are oriented in the opposite direction. As such, the V-shaped cross-links 33 on one outer row point in a longitudinal direction opposite to the V-shaped cross-links 33 in the other two rows. As the stent 10 is diametrically expanded, each V-shaped cross-link 33 bends and straightens about the apex or fulcrum 34 so that the stent 10 maintains its generally tubular shape. The central lumen of the stent 10 widens, but the longitudinal struts 28 inhibit longitudinal foreshortening thereby maintaining the overall length of the stent 10. Since the stent 10 is plastically deformed, there is very little recoil and the stent 10 resists being recompressed.

The V-shaped cross-links 33 are dimensioned with relatively short legs 35 as compared to the relatively longer legs, 21 and 22, of the parabolic end links 11. The relatively long moment arm provided by the parabolic end links 11 positioned at the outer ends of the stent 10 ensure that radial flexibility is greatest at the ends, 18 and 19, of the stent 10 and progressively less flexible toward the center 31 of the stent 10. The central cross-links 33 deform about a shorter moment arm and are therefore more rigid. As such, the ends, 18 and 19, of the stent 10 have the ability to move more freely with the vessel during vessel contraction and expansion, thereby minimizing flow disturbance and stress concentration in the artery wall.

In a particular embodiment, the stent 10 may be fabricated from a single piece of continuous tube with no welds or solder points. For example, a 316L grade seamless stainless steel tube with an outer diameter of 0.2" (4.8 mm), a nominal wall thickness of 0.012" (0.3 mm), and an overall length of 1.33" (32.5 mm) may be used. The stent 10 when expanded may reach an outer diameter on the order of 0.47" (12 mm). Wire electrical discharge machining (EDM) can be used for removing sections of the tubing to extremely high precision without creating burrs or deformations. The wire diameter for cutting can be approximately 0.010" (0.254 mm) resulting in corners that are radiused to 0.005" (0.127 mm). Using this method the stent 10 can be made having a general tubular structure comprising a thin-walled lattice frame with openings in the frame. After full expansion, the stent 10 can assume a final diameter of approximately 0.471" (12.0 mm) or 2.5 times its original diameter. Alternatively, the stent 10 can be fabricated in its expanded configuration and compressed prior to deployment. Additionally, the stent 10 does not have to be fabricated from a single piece of continuous tube. For example, the longitudinal struts 28 and/or the cross-links 33 can be made separately from the end links 11 and attached using, for example, laser welding techniques.

Construction of the stent 10 is not limited to stainless steel. The stent 10 can also be made from any material which is compatible with the human body and any bodily fluids that the stent 10 may contact. However, the stent 10 must be made from a material that allows for expansion of the stent 10 and must be able to maintain its expanded shape while disposed within the lumen of the body passage. In addition to stainless steel, suitable materials for construction of the stent 10 may include tantalum and titanium.

The stent 10 can also be fabricated from a memory metal such as nitinol, such as the stent 10 depicted in FIGS. 1–3. When the stent 10 is manufactured from a memory metal material, the stent 10 is preferably manufactured to be in its expanded configuration when the stent 10 is at body temperature and in its collapsed configuration at some lower temperature. When the stent 10 is constructed from a memory metal such as nitinol, the stent 10 responds to temperature changes by automatically expanding from a reduced diameter to a final expanded configuration within the vessel. The stent 10 is deployed at the lower temperature and is then allowed to self expand as the stent approaches body temperature.

The stent 10 can be expanded from the inside when deployed at the target location using a balloon-type catheter delivery system. For example, the stent 10 can be mounted on a 0.315" (8 mm) diameter balloon (1.57" (4 cm) in length) which is attached to the end of a catheter. The stent 10 can then be positioned in the desired vessel using, for example, fluoroscopic guidance to insure proper placement of the stent 10. The stent 10 can then be expanded by inflating the balloon uniformly. A pressure of about 10 atmospheres is usually sufficient to expand the stent 10 to its desired larger diameter. However, the pressure should be adjusted to expand the stent 10 to an appropriate final diameter for the specific vessel within which the stent 10 is being deployed.

While the stent 10 may be deployed as a "stand alone" device, the stent 10 may also be effectively used as a vascular endograft by attaching a segment of vein, preferably an autologous vein or a synthetic graft material within the central lumen of the stent 10. Preferably, an autologous vein segment is utilized to provide an endothelial layer as a lining for the lumen of the stent 10.

Figure 4:
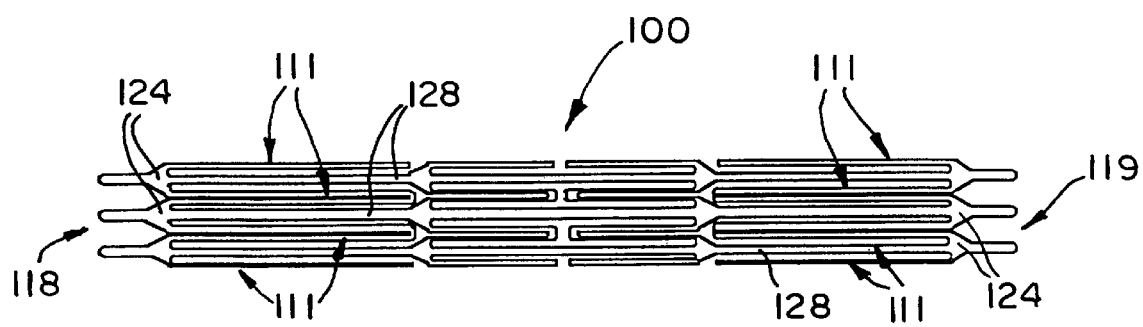
FIG. 4 is an enlarged, side elevational view of a stent in accordance with a second embodiment of the present invention shown in its unexpanded configuration.
Figure 5:
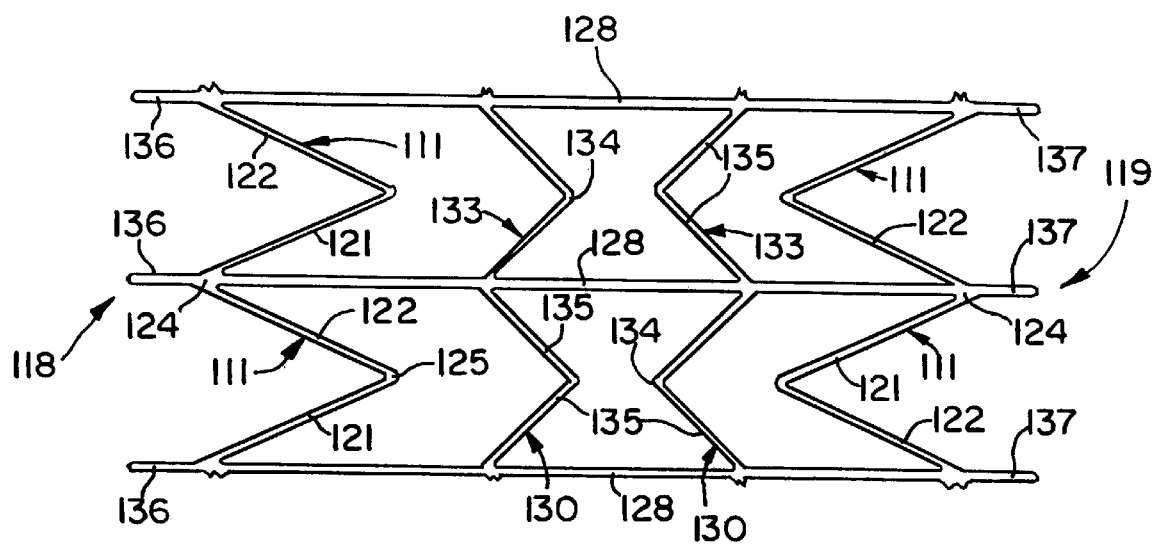
FIG. 5 is a partial cut-away view of the stent of FIG. 4 shown in a flattened, expanded configuration obtained by cutting the stent along longitudinal cutting planes.

An alternate embodiment of a stent 110 in accordance with the present invention is shown in FIGS. 4 and 5. The stent 110 comprises V-shaped end links 111 instead of the parabolically shaped end links 11 of stent 10 shown in FIGS. 1–3. The V-shaped end links provide a fulcrum at the apex 125 of the V-shape. Each V-shaped end link 111 of stent 110 is connected to its adjacent end links 111 at junctions 124 formed near the outer ends of the longitudinal struts 128. The ends, 136 and 137, of the longitudinal struts 128 may extend beyond the junctions 124 at the ends, 118 and 119, of the stent 110. In addition, the stent 110 differs from the stent 10 described in reference to FIGS. 1–3 in that the stent 110 comprises only two rows of circumferential links 130 instead of three. The V-shaped cross-links 133 are disposed so that the apex 134 of each V-shaped cross-link 133 points longitudinally inward from the ends of the stent with the apex 134 of each cross-link 133 in one row longitudinally opposing the apex 134 of a cross-link 133 in the other row. The legs 135 of the V-shaped cross-links 133 are relatively shorter than the legs, 121 and 122, of the V-shaped end-links 111 to provide greater radial flexibility at the ends, 118 and 119, of the stent 110 for improved compliance matching with the vessel.

Figure 6:
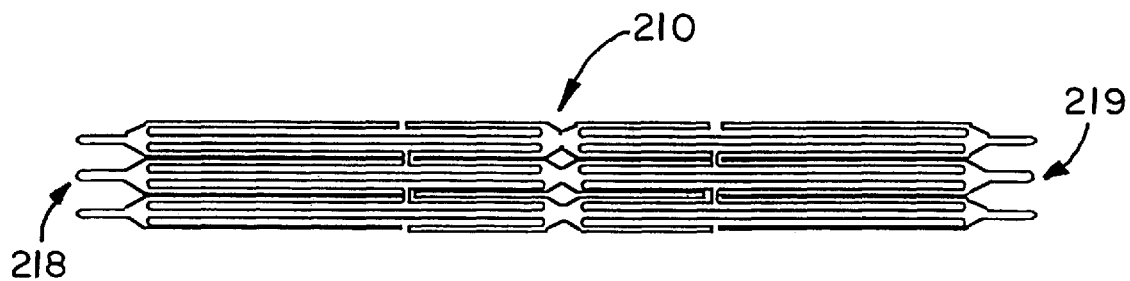
FIG. 6 is an enlarged, side elevational view of a stent in accordance with a third embodiment of the present invention shown in its unexpanded configuration.
Figure 7:
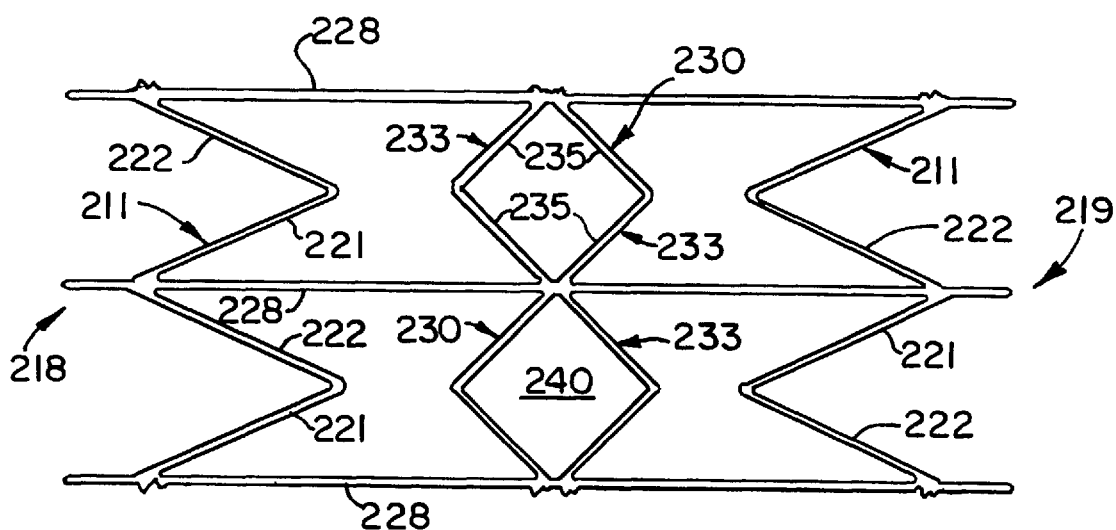
FIG. 7 is a partial cut-away view of the stent of FIG. 6 shown in a flattened, expanded configuration obtained by cutting the stent along longitudinal cutting planes.

Yet another alternate embodiment of a stent 210 in accordance with the present invention is shown in FIGS. 6 and 7. The stent 210 is similar to the stent 110 described in reference to FIGS. 4 and 5 except that the V-shaped cross-links 233 of the circumferential links 230 are disposed to point outward toward the ends, 218 and 219, of the stent 210. In addition, the legs 235 of the cross-links 233 in one row connect with the longitudinal struts 228 at the same general location as the legs 235 of the opposing cross-links 233 in the other row. As such, a plurality of rhomboidal or diamond-shaped spaces 240 are formed between the opposing cross-links 233 that interconnect adjacent longitudinal struts 228. Again, the legs 235 of the cross-links 233 are much shorter than the legs, 221 and 222, of the end links 211.

Figure 8:
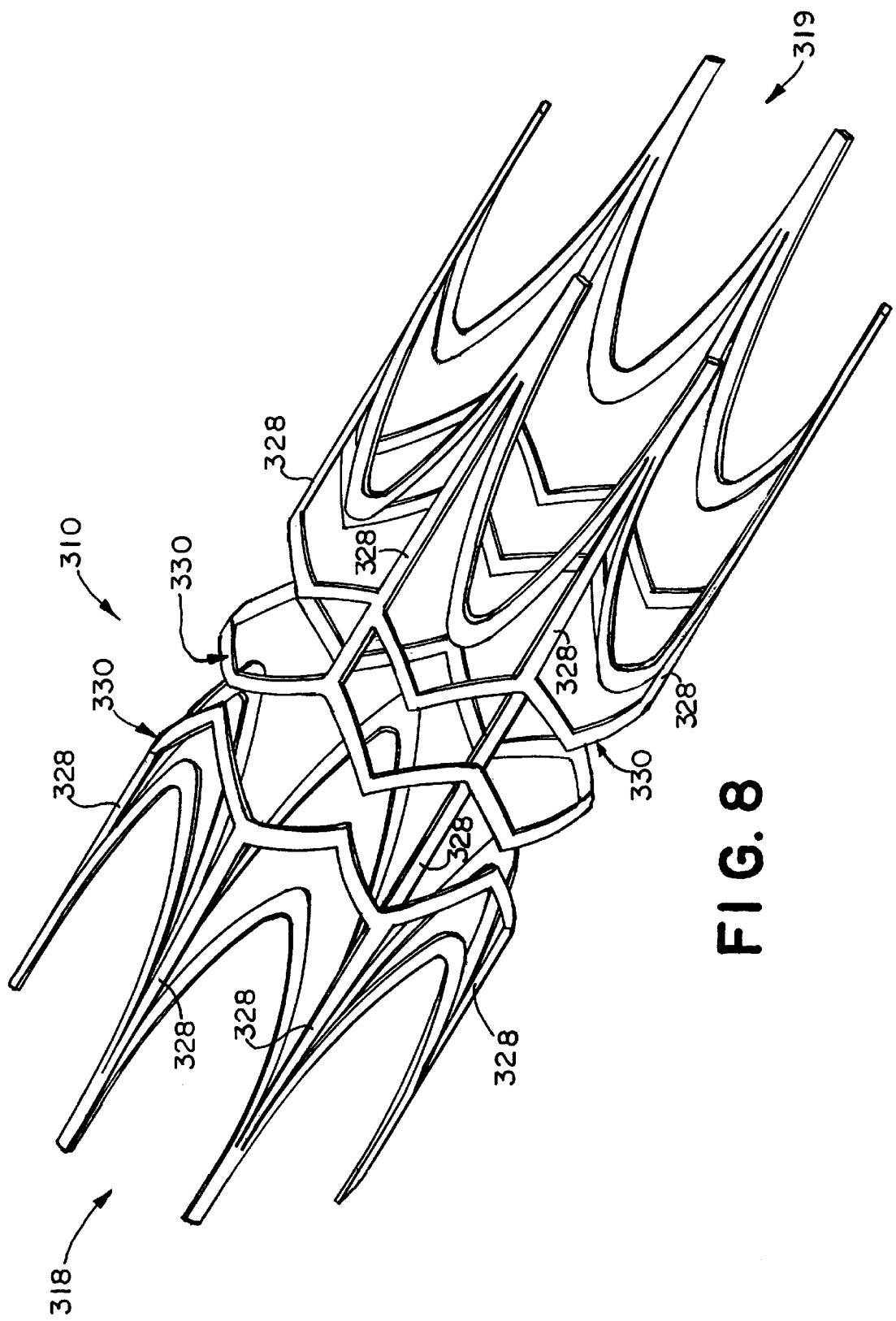
FIG. 8 is an enlarged perspective view of a stent in accordance with a fourth embodiment of the present invention shown in an expanded configuration.
Figure 9:
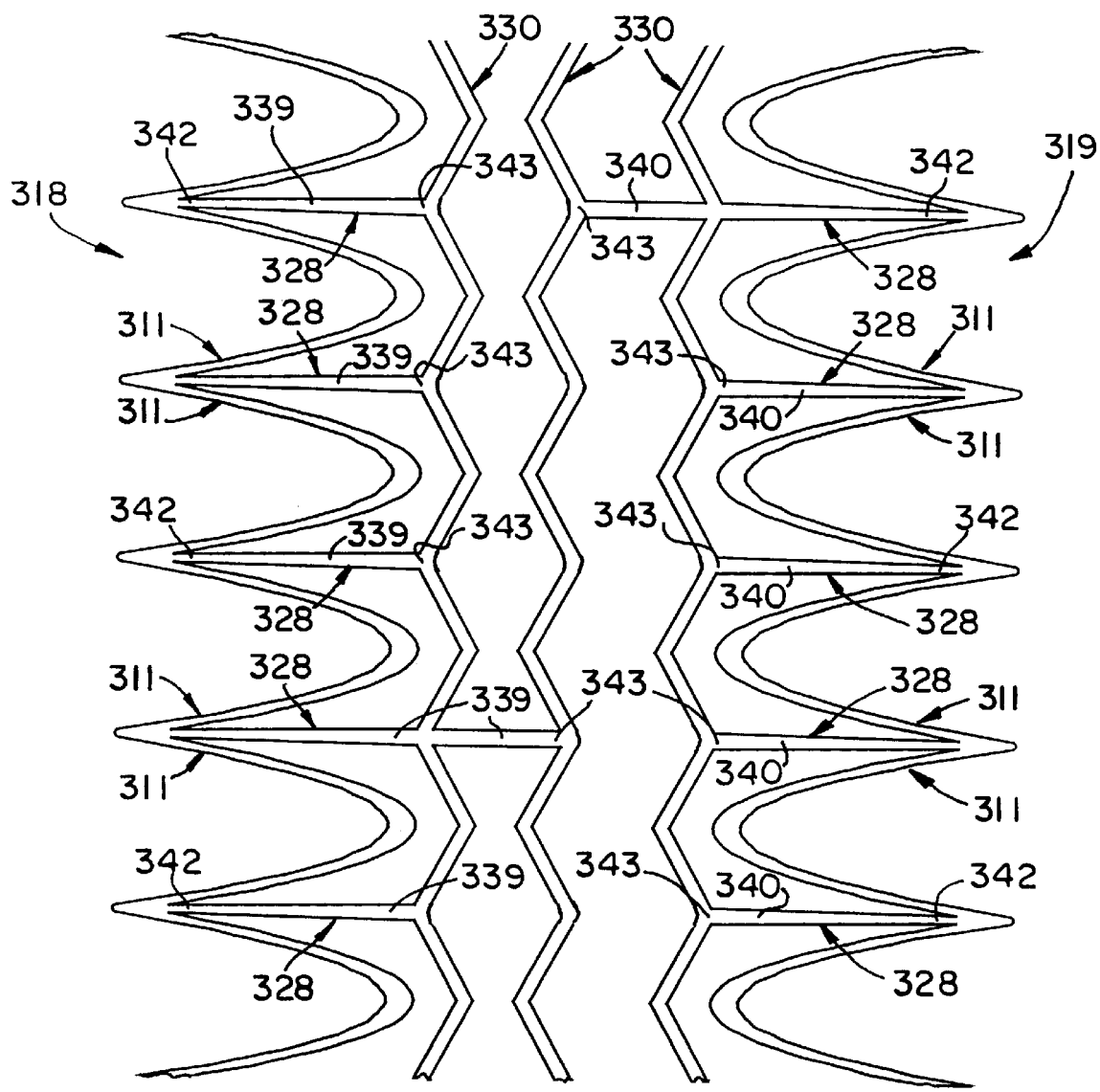
FIG. 9 is a partial cut-away view of the stent of FIG. 8 shown in a flattened, expanded configuration obtained by cutting the stent along longitudinal cutting planes.

Still another alternate embodiment of a stent 310 in accordance with the present invention is shown in FIGS. 8 and 9. The stent 310 is similar to the stent 10 described in reference to FIGS. 1–3 except that the longitudinal struts 328 do not extend from one end 318 of the stent 310 to the other end 319 of the stent 310. Instead, portions of the longitudinal struts 328 between adjacent circumferential links 330 are missing to provide the stent 310 with greater radial flexibility. In particular, as best seen in FIG. 9, the longitudinal struts 328 comprise a plurality of first bars 339 positioned at the first end 318 of the stent 310 and a plurality of second bars 340 symmetrically positioned at the second end 319 of the stent 310. First and second bars, 339 and 340, each have two ends, 342 and 343. One end 342 of the first bars 339, in the form of strut segments, is connected to two adjacent end links 311 at the first end 318 of the stent 310. The other end 343 of the first bars 339 is connected to one of the circumferential links 330. Further, one end 342 of each second bar 340, in the form of a strut segment, is connected to two adjacent end links 311 at the second end 319 of the stent 310 and the other end 343 of each second bar 340 is connected to one of the circumferential links 330. As shown in FIG. 9, one bar 339, 340 at each respective end of the stent is longer than the other bars at the same end of the stent and is disposed to extend to the central row of the circumferential links 330 whereas the remaining bars at the first end only extend to the row of circumferential links adjacent the first end and the remaining bars at the second end only extend to the row of circumferential links adjacent the second end of the stent. These longer bars are symmetrically disposed on opposite sides of the stent. Accordingly, the longitudinal struts 328 are arranged such that only one longitudinal strut 328 extends between the center row of circumferential links 330 and the row of circumferential links 330 nearest the first end 318 of the stent 310 and only one longitudinal strut 328 extends between the center row of circumferential links 330 and the row of circumferential links 330 nearest the second end 319 of the stent 310.

It will be recognized by those skilled in the art that changes or modifications may be made to the above-described embodiments without departing from the broad inventive concepts of the invention. It should therefore be understood that this invention is not limited to the particular embodiments described herein, but is intended to include all changes and modifications that are within the scope and spirit of the invention as set forth in the claims.

What is claimed is:

1. An expandable, generally tubular, intraluminal stent, having two ends and a center portion, for insertion within the lumen of a vessel, comprising:
   a. a plurality of rigid longitudinal struts oriented generally parallel to one another about a central axis of the tubular stent;
   b. a plurality of end links connected between ends of the longitudinal struts, each end link having a first and second leg joined at a fulcrum with the first leg connected with an end of one longitudinal strut and the second leg connected with an end of an adjacent longitudinal strut so that moment arms provided by the first and second legs permit radial flexibility of the stent to gradually decrease from the ends of the stent toward the center portion of the stent; and
   c. a plurality of deformable cross-links circumferentially connecting longitudinal struts at the center portion of the stent, each cross-link having first and second ends disposed at an acute angle with respect to a longitudinal axis of the longitudinal struts to permit the stent to expand upon deformation of the cross-links from a first smaller diameter into a second larger diameter, the deformed cross-links being more rigid than the end links to provide increased rigidity at the center portion of the expanded stent.

2. The stent in accordance with claim 1 wherein the first end of each end link is connected to the second end of an adjacent end link.

3. The stent in accordance with claim 2 wherein the first end of each end link is connected to The second end of an adjacent end link at a junction generally at the end of the stent.

4. The stent in accordance with claim 1 wherein the end links are parabolically shaped.

5. The stent in accordance with claim 4 wherein the end links have a width which is greatest at the fulcrum and tapers towards the first and second ends.

6. The stent in accordance with claim 1 wherein the cross-links include a pair of legs joined at a fulcrum.

7. The stent in accordance with claim 6 wherein the cross-links are V-shaped.

8. The stent in accordance with claim 1 wherein the end links include a pair of legs joined at a fulcrum.

9. The stent in accordance with claim 8 wherein the end links are V-shaped.

10. The stent in accordance with claim 8 wherein the end links have a width which is greatest at the fulcrum and tapers towards the ends of the legs.

11. The stent in accordance with claim 8 wherein the cross-links include a pair of legs joined at a fulcrum.

12. The stent in accordance with claim 11 wherein the cross-links are V-shaped.

13. The stent in accordance with claim 11 wherein the legs of the cross-links are shorter relative to the legs of the end links.

14. The stent in accordance with claim 1 wherein the longitudinal struts extend generally from one end of the stent to the other end of the stent to inhibit longitudinal foreshortening of the stent during expansion of the stent.

15. The stent in accordance with claim 14 wherein the cross-links circumferentially connect adjacent longitudinal struts at the center portion of the stent.

16. The stent in accordance with claim 14 wherein the first end of each end link is connected to the second end of an adjacent end link.

17. The stent in accordance with claim 16 wherein the first end of each end link is connected to the second end of an adjacent end link at a junction generally at the end of the stent.

18. The stent in accordance with claim 14 wherein the end links are parabolically shaped.

19. The stent in accordance with claim 18 wherein the end links have a width which is greatest at the fulcrum and tapers towards the first and second ends.

20. The stent in accordance with claim 14 wherein the cross-links include a pair of legs joined at a fulcrum.

21. The stent in accordance with claim 20 wherein the cross-links are V-shaped.

22. The stent in accordance with claim 14 wherein the end links include a pair of legs joined at a fulcrum.

23. The stent in accordance with claim 22 wherein the end links are V-shaped.

24. The stent in accordance with claim 22 wherein the end links have a width which is greatest at the fulcrum and tapers towards the ends of the legs.

25. The stent in accordance with claim 22 wherein the cross-links include a pair of legs joined at a fulcrum.

26. The stent in accordance with claim 25 wherein the cross-links are V-shaped.

27. The stent in accordance with claim 25 wherein the legs of the cross-links are shorter relative to the legs of the end links.

28. The stent in accordance with claim 1 wherein the cross-links are arranged to define a plurality of deformable circumferential links.

29. The stent in accordance with claim 1 wherein at least one of the longitudinal struts extends only part of the distance between the two ends of the stent.

30. The stent in accordance with claim 29 wherein at least one of the longitudinal struts extends no more than about half the distance between the two ends of the stent.

31. The stent in accordance with claim 29 wherein at least one of the longitudinal struts comprises a plurality of bars.

32. The stent in accordance with claim 31 wherein at least one longitudinal strut comprises a first bar positioned at the first end of the stent and a second bar symmetrically positioned at the second end of the stent, the first and second bars each having two ends with one end of the first bar being connected to the end links at one end of the stent, the other end of the first bar being connected to one of the circumferential links, one end of the second bar being connected to the end links at the other end of the stent, and the other end of the second bar being connected to a different circumferential link.

33. The stent in accordance with claim 29 wherein the first end of each end link is connected to the second end of an adjacent end link.

34. The stent in accordance with claim 33 wherein the first end of each end link is connected to the second end of an adjacent end link at a junction generally at the end of the stent.

35. The stent in accordance with claim 29 wherein the end links are parabolically shaped.

36. The stent in accordance with claim 35 wherein the end links have a width which is greatest at the fulcrum and tapers towards the first and second ends.

37. The stent in accordance with claim 29 wherein the cross-links include a pair of legs joined at a fulcrum.

38. The stent in accordance with claim 37 wherein the cross-links are V-shaped.

39. The stent in accordance with claim 29 wherein the end links include a pair of legs joined at a fulcrum.

40. The stent in accordance with claim 39 wherein the end links are V-shaped.

41. The stent in accordance with claim 39 wherein the end links have a width which is greatest at the fulcrum and tapers towards the ends of the legs.

42. The stent in accordance with claim 39 wherein the cross-links include a pair of legs joined at a fulcrum.

43. The stent in accordance with claim 42 wherein the cross-links are V-shaped.

44. The stent in accordance with claim 42 wherein the legs of the cross-links are shorter relative to the legs of the end links.

45. An expandable, generally tubular, intraluminal stent, having a longitudinal axis, for insertion within the lumen of a vessel, comprising a. at least one rigid longitudinal strut oriented generally parallel to a central axis of the stent:

a. a rigid center portion to intenially support the vessel; and b. end sections joined to the rigid center portion having changing flexibility along the longitudinal axis of the stent, the end sections having greater radial flexibility at outer ends of the stent with the radial flexibility gradually decreasing toward the center portion.

46. The stent in accordance with claim 45 wherein the radial flexibility at the outer ends of the stent is matched to the flexibility of the vessel.

47. An expandable, generally tubular, intraluminal stent, having two ends and a center portion, for insertion within the lumen of a vessel, comprising:

a. a plurality of end links disposed in a ring at each end of the tubular stent, a first end of each end link being connected to a second end of an adjacent end link, each end link having a first and a second leg joined at a fulcrum so that moment arms provided by the first and second legs permit flexibility of the stent to gradually decrease from the ends of the stent toward the center portion of the stent;

b. at least one rigid longitudinal strut oriented generally parallel to a central axis of the stent, the longitudinal strut extending from the ring of end links at one end of the stent to the ring of end links at the other end of the stent; and c. at least one circumferential link attached to the longitudinal strut at about the center portion of the stent to permit the stent to expand upon deformation of the circumferential link from a first smaller diameter into a second larger diameter.

* * * * *

UNITED STATES PATENT AND TRADEMARK OFFICE
CERTIFICATE OF CORRECTION

PATENT NO. : 6,206,910 B1
DATED : March 27, 2001
INVENTOR(S) : Joel L. Berry and James E. Moore It is certified that error appears in the above-identified patent and that said Letters Patent is hereby corrected as shown below:

Column 5,
Line 10, "0.471" should read -- 0.47 --.

Column 7,
Line 42, "The second end" should read -- the second end --.

Column 9,
Line 24, "comprising a. at least one" should read
    -- comprising:
        a. at least one --.
Line 25, "stent:" should read -- stent; --.
Line 26, "a." should read -- b. --.
Line 26, "intenially" should read -- internally --.
Line 28, "b." should read -- c. --.

Signed and Sealed this

Twelfth Day of October, 2004

JON W. DUDAS
*Director of the United States Patent and Trademark Office*